United States Patent
Munroe et al.

(10) Patent No.: US 6,805,300 B2
(45) Date of Patent: Oct. 19, 2004

(54) AUTOMOTIVE AROMATHERAPY DIFFUSER

(75) Inventors: Kevin J. Munroe, Fairfield, IA (US); Jeffrey L. Smith, Fairfield, IA (US); Cheriyan B. Thomas, New Albany, OH (US); Jeffrey J. Grote, Columbus, OH (US); Bradley D. Pesu, Gahanna, OH (US); Richard R. Ruffolo, Reynoldsburg, OH (US)

(73) Assignee: Aeron North America, LLC, Fairfield, IA (US)

( * ) Notice: Subject to any disclaimer, the term of this patent is extended or adjusted under 35 U.S.C. 154(b) by 255 days.

(21) Appl. No.: 10/083,171

(22) Filed: Feb. 26, 2002

(65) Prior Publication Data

US 2003/0160106 A1 Aug. 28, 2003

(51) Int. Cl.$^7$ ............................................. A24F 25/00
(52) U.S. Cl. ............................. 239/34; 239/53; 239/60
(58) Field of Search ............................ 239/34, 71, 53, 239/60

(56) References Cited

U.S. PATENT DOCUMENTS

| | | | |
|---|---|---|---|
| 2,898,649 A | * | 8/1959 | Murray ........................ 422/125 |
| 4,473,086 A | * | 9/1984 | Thaler et al. ................ 132/229 |
| 4,968,456 A | * | 11/1990 | Muderlak et al. ........... 422/122 |
| 5,394,506 A | * | 2/1995 | Stein et al. .................. 392/395 |
| 6,264,548 B1 | * | 7/2001 | Payne et al. ................. 454/157 |
| 6,374,044 B1 | * | 4/2002 | Freidel ........................ 392/390 |
| 6,471,193 B2 | * | 10/2002 | Cole Warren ................ 261/27 |

* cited by examiner

Primary Examiner—Christopher S. Kim

(57) ABSTRACT

An automotive air freshener for insertion into a cigarette lighter socket of a vehicle has an elongated housing having first and second ends and opposite sides. First and second electrical contacts are in the first end of the housing and are adapted for insertion into the cigarette lighter socket so that the first and second electrical contacts can be in electrical contact with the socket. An internal circuit board has a switch and an operating current in contact with the first and second electrical contacts. Power is conveyed through the electrical contacts to the circuit board to provide heat at varying degrees to heat a fragrance pad and to operate a fragrance emitting phenomenon. A cover is connected to the circuit board to protect a user from burns.

7 Claims, 3 Drawing Sheets

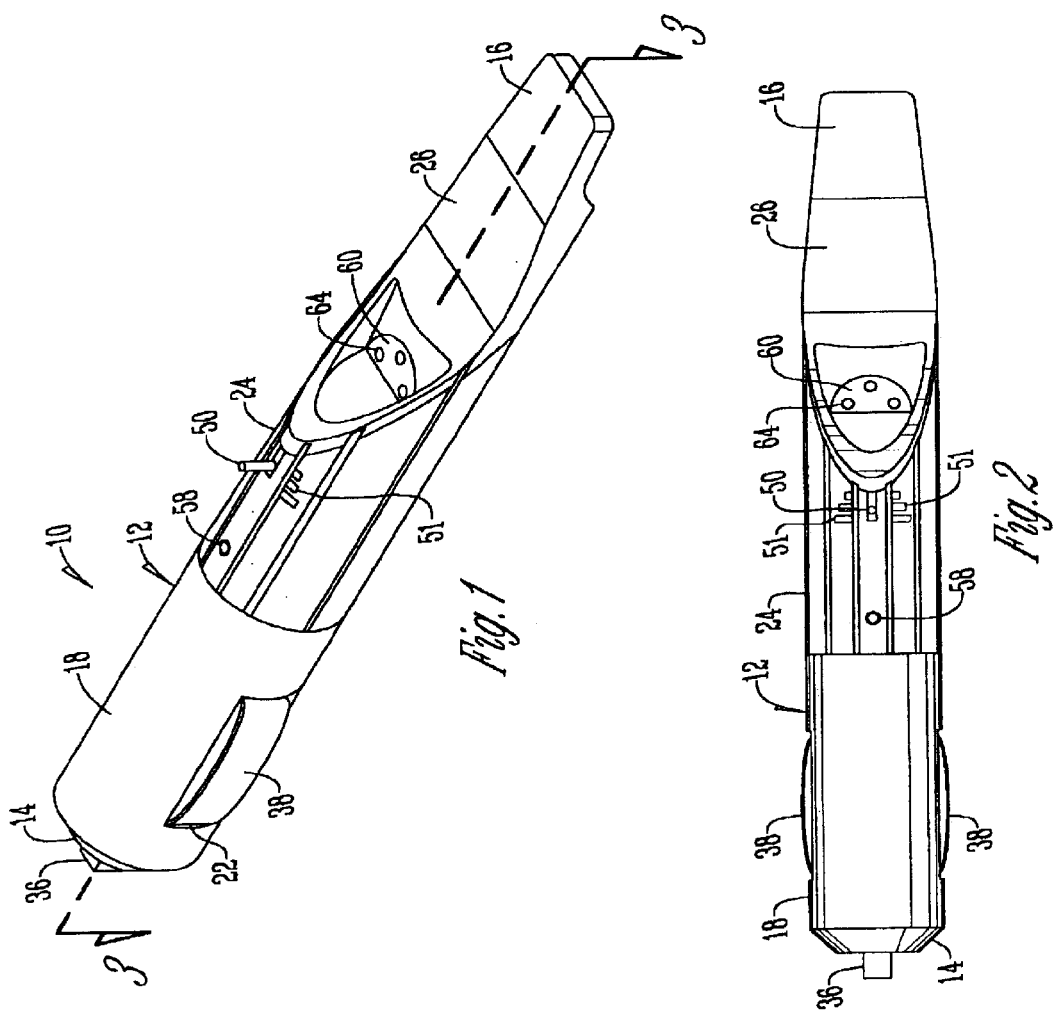

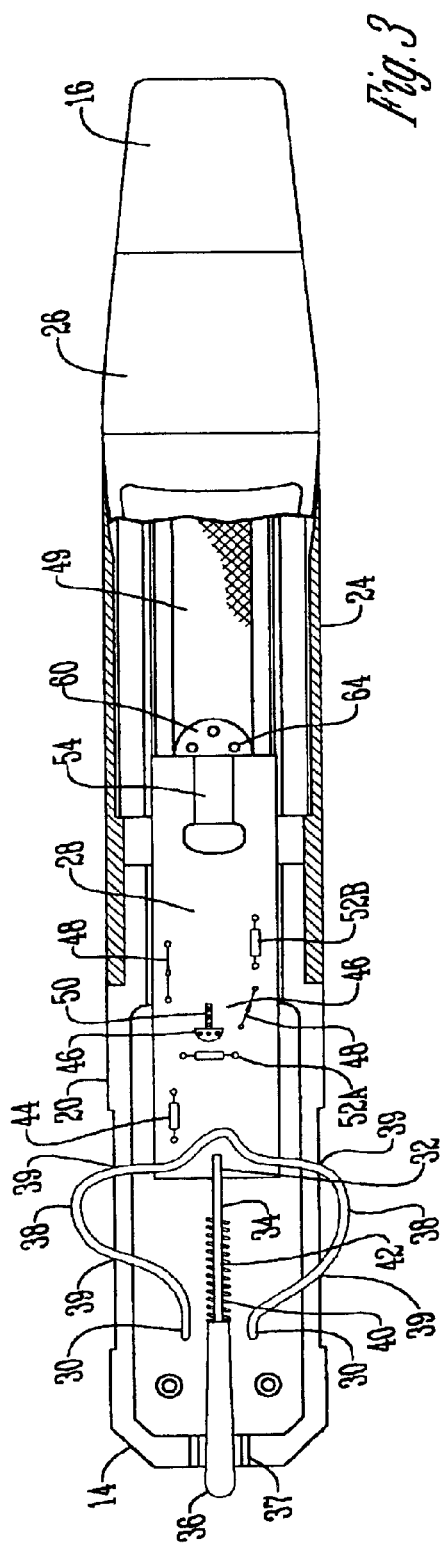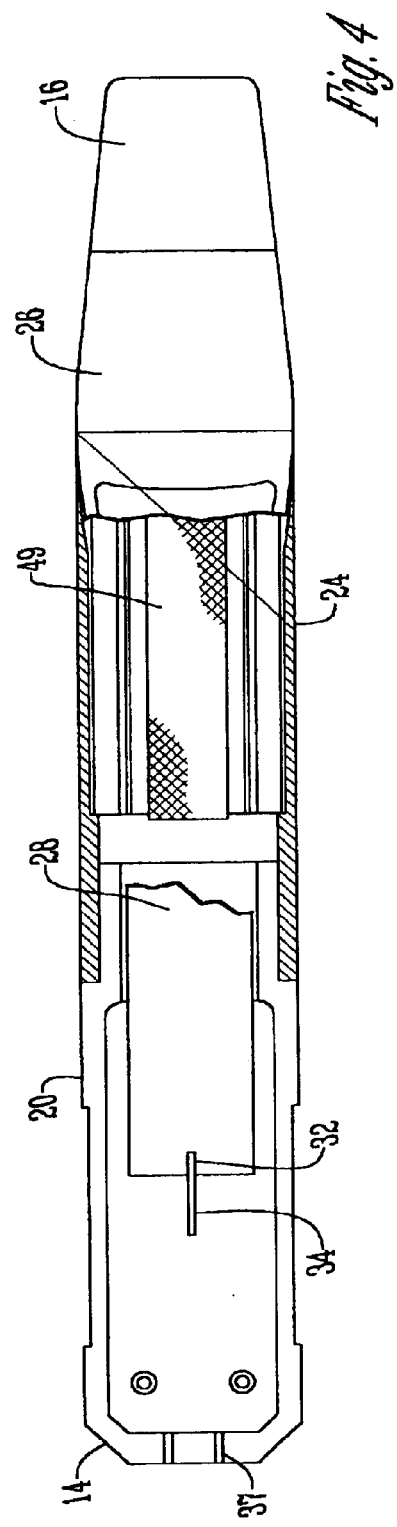

AUTOMOTIVE AROMATHERAPY DIFFUSER

BACKGROUND OF THE INVENTION

Automotive aromatherapy diffusers are used in automobiles to improve the fragrance of the air within the passenger compartment. They are normally plugged into the empty cigarette lighter socket of a conventional automobile. The electrical system of the automobile, among other things, energizes an internal resistor which provides heat to a fragrance laden pad. The heat from the resistor energizes the fragrance in the pad and dispels the fragrance to the interior of the passenger compartment.

One of the problems of such a device is that the heat from the resistor is not adjustable in present diffusers. The inability to adjust the heat leads not only to the inefficient diffusion of the oils in the fragrance laden pad, but also in circuit boards presently used, the risk of system failure and even fire are always present. In addition, present diffusers have no cover to surround the heated pad to prevent one from touching the pad and being burned.

It is therefore a principal object of this invention to provide an automotive aromatherapy diffuser that is capable of regulating the heat provided to the fragrance pad in a safe and efficient manner.

Another object of this invention is to avoid operational malfunction.

A further object of this invention is to provide an automotive aromatherapy diffuser that is safe to use and operate.

These and other objects will be apparent to those skilled in the art.

SUMMARY OF THE INVENTION

An automotive air freshener for insertion into a cigarette lighter socket of a vehicle has an elongated housing having first and second ends and opposite sides. A first electrical contact is in the first end of the housing and protrudes from the inside to the outside of the housing. Second electrical contacts are on the opposite sides of the first end and protrude from the inside to the outside of the housing. The cross-sectional size of the first end of the housing is adapted for insertion into the cigarette lighter socket so that the first and second electrical contacts can be in electrical contact with the socket.

The first electrode control has an internal end that is connected to an internal electrode by an elongated conductive spring. Power is conveyed through the electrodes and the spring to energize several safe electrical control components within the housing to provide heat at varying temperatures to a fragrance laden pad and to operate the fragrance emitting phenomenon. A cover is connected to the electrical components and surrounds the pad to protect against injury.

BRIEF DESCRIPTION OF THE PREFERRED EMBODIMENT

FIG. 1 is a perspective view of the diffuser of this invention;

FIG. 2 is a top plan view thereof;

FIG. 3 is an enlarged scale horizontal cross-sectional view thereof taken on line 3—3 of FIG. 1;

FIG. 4 is a view similar to that of FIG. 3 but with the external electrical conductors removed therefrom;

BRIEF DESCRIPTION OF THE PREFERRED EMBODIMENTS

Figure 5:
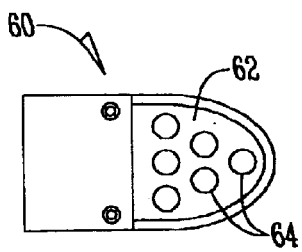
FIG. 5 is a top plan view of a cover.
Figure 6:
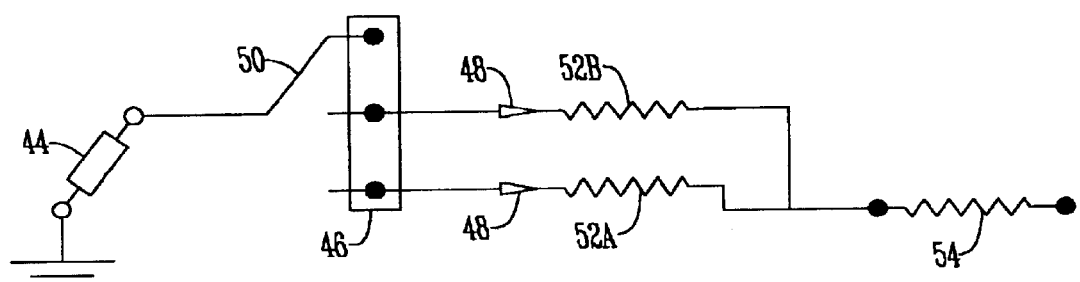
FIG. 6 is a circuit diagram of the electrical components of the circuit board.

The diffuser 10 has a body 12 which has a front or forward end 14 and a rearward end 16. Body 12 includes split cylindrical housing elements 18 and 20 which fit together and comprise a forward cylindrical housing area. The housing elements 18 and 20 unite at horizontal seam 22. The housing elements 18 and 20 are made of Nylon 66 or any other material that has similar heat and solvency characteristics, as well as a higher impact strength. A hollow sleeve 24 receives the rearward ends of housing elements 20 and holds them in rigid assembled contact with each other. A rear housing 26 is slidably received in the other end of sleeve 24.

An internal conventional circuit board 28 (FIGS. 3–5) has two parallel side electrodes 30 mounted thereon with a center electrode 32 mounted there between (FIG. 4). The center electrode 32 has a forwardly extending connector portion 34 thereon.

An external electrode 36 (best shown in FIG. 3) on the forward end 14 of body 12 is received in notch 37 of housing element 18 and terminates in an inner end which comprises a connector portion 40 (FIG. 5). The connector portions 40 and 34 of electrodes 36 and 32, respectively, are spaced approximately ⅜". An elongated compression spring 42 is slightly compressed and receives in its hollow opposite ends each of the connecting portions 34 and 40. Spring 42 electrically connects the electrodes 34 and 40 so as to relieve any possible stress or vibrations that might be otherwise imposed on the electrical connection. This results from the resiliency of the spring 42. Side electrodes 38 are mounted in notches 39 and are internally connected to side electrodes 30.

A fuse 44, an LED 46, diodes 48, a switch 50, heat controlling resistors 52A and 52B and heat emitting resistor 54 are mounted on circuit board 28 in conventional fashion and are electrically connected to each other. For best results, preferred is the use of a 0.5 amp fuse 44, a 0.3 mm green/amber dual tone LED 46, model 4148 diodes 48, a three position switch 50, a 1×¼ w 820 ohm carbon film resistor 52A, a 1×¼ w 56 ohm carbon film resistor 52B, and a 1 w 200 ohm metal oxide resistor 54. On housing element 20, aligned with the switch 50 are indicia 51 to indicate the switch setting. A pad 56 is in the rear housing 26 and is conventionally saturated with a fragrance solution which permeates the air when the resistor 54 emanates operational heat. Transparent pins 58 are used to secure the sleeve 24 to the housing parts.

Connected to the circuit board 28 and surrounding a portion of the heat emitting resistor 54 is a cover 60. The cover 60 has a bottom 62 with a plurality of holes 64 to maximize the airflow around the resistor 54 to provide optimal scent diffusion and an open top (not shown) so that the cover does not obstruct the heat from resistor 54 that is directed toward the pad 56. The cover 60 can be connected in any conventional manner but it is preferred that it is heat welded to the circuit board. Further, the cover 60 is made of Nylon® 66 or any other material that has similar heat resistant characteristics.

In operation, the diffuser is inserted into a conventional cigarette lighter socket of a vehicle which connects external electrodes 36 and 38 to the conductive portions of the cigarette lighter socket. This serves to convey electrical power through the electrode 36, through the spring 42, into the conductor 34 and thence into the circuit board. The current flows to the circuit board 28 and the control circuit through fuse 44 to switch 50 and then to LED 46. In the off setting of switch 50 current flow stops. In the low setting of switch 50 current flows through diode 48 to resistor 52B and then to resistor 54 where heat is provided to the pad 56. In the high setting of switch 50 current flows through a diode 48 to resistor 52A and then to resistor 54 where heat is provided to the pad 56. All this is in conjunction with the electrical contacts provided by electrodes 38 with their connection to the two side electrodes 30.

The circuit board 28 and the cover 60 provide all of the beneficial results described heretofore. It is, therefore, seen that this invention will achieve at least all of its stated objectives.

As various changes could be made in the above constructions without departing from the scope of the invention, it is intended that all matter contained in the above description or shown in the accompanying drawings shall be interpreted as illustrative and not in a limiting sense.

What is claimed is:

1. An automotive air freshner for insertion into a cigarette lighter socket of an auto operatively connected to a source of electrical power, comprising:

an elongated housing having first and second ends and opposite sides, a first electrical contact in the first end of said housing and protruding from the inside to the outside of the housing, second electrical contacts on the opposite sides of said first end and protruding from the inside to the outside of the housing, the first end of the housing being adapted for insertion into the cigarette lighter socket so that the first and second electrical contacts can be in electrical contact with the socket, an elongated circuit board in the housing extending towards the first and second ends connected to the first and second electrical contacts and including a control circuit with a multi-position circuit with a multi-position switch that provide varying degrees of heat to an electrical heater element, an aromatic fragrance means in said housing, and the electrical heater element positioned adjacent the aromatic fragrance means to heat the fragrance means to produce an aromatic fragrance.

2. The device of claim 1 wherein the switch has an off, a low and a high position.

3. The device of claim 1 wherein the control circuit includes a fuse connected to the switch, which is connected to an LED, which is connected to diodes, which are electrically connected to resistors and the electrical heater element to provide varying degrees of heat to the fragrance means based on the position of the switch.

4. The device of claim 1 wherein a cover is connected to the circuit board and surrounds a portion of the electrical heater element in said housing.

5. The device of claim 1 wherein the switch has an off, a low and a high position.

6. The device of claim 1 wherein the control circuit includes a fuse connected to the switch, which is connected to an LED, which is connected to diodes, which are electrically connected to resistors and the electrical heater element to provide varying degrees of heat to the fragrance means based on the position of the switch.

7. An automotive air freshner for insertion into a cigarette lighter socket of an auto operatively connected to a source of electrical power, comprising:

an elongated housing having first and second ends and opposite sides, a first electrical contact in the first end of said housing and protruding from the inside to the outside of the housing, second electrical contacts on the opposite sides of said first end and protruding from the inside to the outside of the housing, the first end of the housing being adapted for insertion into the cigarette lighter socket so that the first and second electrical contacts can be in electrical contact with the socket, an elongated circuit board in the housing extending towards the first and second ends connected to the first and second electrical contacts and including a control circuit with a multi-position switch that provide varying degrees of heat to an electric heater element, an aromatic fragrance means in said housing, the electrical heater element positioned adjacent the aromatic fragrance means to heat the fragrance means to produce an aromatic fragrance, and a cover that is connected to the circuit board and surrounds a portion of the electrical heater element.

\* \* \* \* \*